United States Patent [19]

Ogura et al.

[11] Patent Number: 4,515,661
[45] Date of Patent: May 7, 1985

[54] PROCESS FOR SEPARATING HIGHLY PURE BUTENE-1 AND BUTENE-2

[75] Inventors: Shunichiro Ogura, Tokyo; Masamichi Soumai, Yokohama, both of Japan

[73] Assignee: Nippon Zeon Co. Ltd., Tokyo, Japan

[21] Appl. No.: 420,871

[22] Filed: Sep. 21, 1982

[30] Foreign Application Priority Data

Oct. 13, 1981 [JP] Japan ................................. 56-163073
Oct. 13, 1981 [JP] Japan ................................. 56-163074

[51] Int. Cl.³ ........................... B01D 3/40; C07C 7/04
[52] U.S. Cl. ......................................... 203/60; 203/14; 203/71; 203/73; 203/78; 203/84; 585/802; 585/809; 585/810; 585/860
[58] Field of Search ............... 585/802, 809, 860, 816, 585/810, 717, 633, 615, 864, 835; 203/57, 58, 14, 71, 73, 60, 50, 78, 84, 62, 44, 28, 74, 75, 80

[56] References Cited

U.S. PATENT DOCUMENTS

| | | | |
|---|---|---|---|
| 2,911,452 | 11/1959 | Broughton | 585/809 |
| 3,013,952 | 12/1961 | Clay | 203/78 |
| 3,232,850 | 2/1966 | Renberg et al. | 203/78 |
| 3,772,158 | 11/1973 | Sarno | 203/62 |
| 4,128,457 | 12/1978 | Barba et al. | 585/860 |
| 4,134,795 | 1/1979 | Howat | 203/60 |
| 4,162,198 | 7/1979 | Stockburger et al. | 203/58 |
| 4,269,668 | 5/1981 | Patel | 203/84 |
| 4,356,339 | 10/1982 | Imaizumi et al. | 585/809 |
| 4,391,677 | 7/1983 | Harris et al. | 203/28 |

FOREIGN PATENT DOCUMENTS 829021 2/1960 United Kingdom ............... 203/62

Primary Examiner—Wilbur Bascomb
Assistant Examiner—Virginia Manoharan
Attorney, Agent, or Firm—Sherman & Shalloway

[57] ABSTRACT

A process for separating highly pure butene-2 and butene-1 from a $C_4$ hydrocarbon fraction containing isobutane, n-butane, butene-1, butene-2, and at least one diolefinic hydrocarbon and/or at least one acetylenic hydrocarbon, which comprises, (1) as a step A, treating the $C_4$ hydrocarbon fraction with a polar solvent to separate it into an overhead product containing isobutane and n-butane and a bottoms product containing butene-1, butene-2, the diolefinic hydrocarbon and/or the acetylenic hydrocarbon, (2) as a step B, introducing the bottoms product from step A into a first distillation column to obtain a fraction containing butene-1, the olefinic hydrocarbon and/or the acetylenic hydrocarbon and purified butene-2, (3) as a step C, introducing the fraction obtained in step B into a second extractive distillation column and treating it with a polar solvent to separate it into an overhead product containing butene-1 and a bottoms product containing the diolefinic hydrocarbon and/or the acetylenic hydrocarbon, or (2') as a step B, introducing the bottoms product from step A into a second extractive distillation column and treating it with a polar solvent to separate it into an overhead product containing butene-1 and butene-2 and a bottoms product containing the diolefinic hydrocarbon and/or the acetylenic hydrocarbon, (3') as a step C, introducing the overhead product from the step B into a first distillation column to obtain butene-1 and purified butene-2, and (4) as a step D, introducing the overhead product or butene-1 obtained in step C into a second distillation column to remove a tiny amount of water and obtain purified butene-1.

3 Claims, 2 Drawing Figures

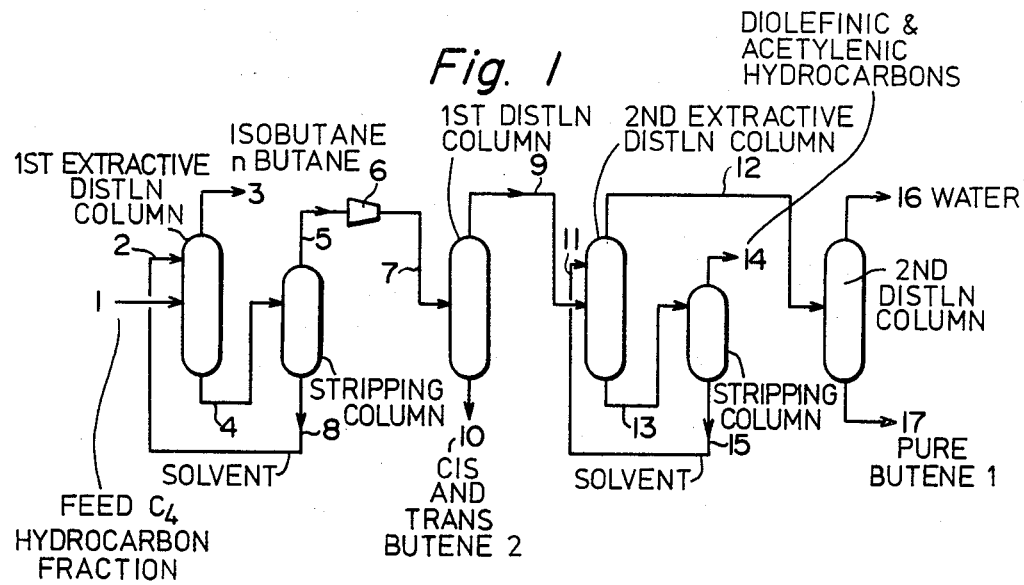
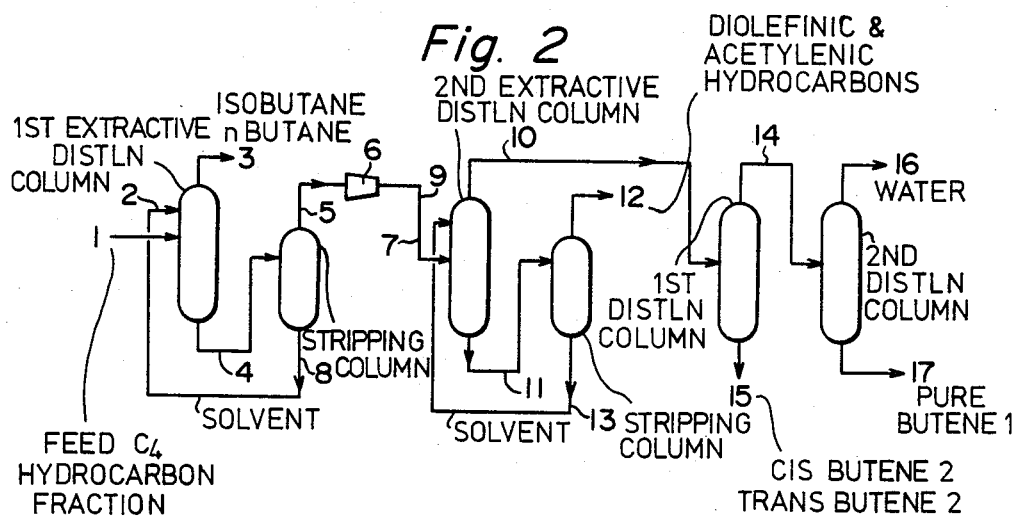

PROCESS FOR SEPARATING HIGHLY PURE BUTENE-1 AND BUTENE-2

This invention relates to a process for separating highly pure butene-1 and butene-2 from a $C_4$ hydrocarbon fraction containing isobutane, n-butane, butene-1, butene-2 and at least one diolefinic or acetylenic hydrocarbon.

Butene-1 of high purity is used as a comonomer in the production of ethylene polymers. Butene-1 for use in this field is required to have such a high purity as illustrated in Table 1 below.

Butene-1 may be polymerized to obtain polybutene-1 which is particularly suitable as a material for hot water pipes in heating systems, etc. because of its excellent high-temperature stress cracking resistance, high-temperature creep resistance and environmental stress cracking resistance.

TABLE 1

Composition of butene-1 for use as a comonomer for production of ethylene polymers Butene-1: more than 99.0% by weight
Butene-2: less than 0.5% by weight
iso-Butene: less than 0.5% by weight
n-Butane: less than 0.5% by weight
1,3-Butadiene: less than 150 ppm
Acetylenes: less than 15 ppm
Water: less than 10 ppm Butene-2 is also a good raw material for maleic anhydride. Furthermore, butadiene can be synthesized by the catalytic oxidative dehydrogenation reaction of butene-2 with a catalyst composed of molybdenum oxide or bismuth oxide as a main ingredient. For example, the article written by L. M. Welch of Petrotex Company of U.S.A. (Hydrocarbon Processing, November 1978, pages 131-136) states that the selectivity to 1,3-butadiene is highest with cis-butene-2, and then with trans-butene-2. Separation of a $C_4$ hydrocarbon fraction by an ordinary distilling method is very disadvantageous from an economic viewpoint because the boiling points of n-butane and trans-butene-2 are very close to each other as shown in Table 2. According to the aforesaid article, if the amount of n-butane in butene-2 is less than 14%, it does not particularly exert adverse effects such as a reduction in selectivity. Since, however, n-butane remains unreacted and gets mixed with the reaction product, the inclusion of a large amount of n-butane makes it necessary to use a large-sized reaction apparatus or worsens the efficiency of a device for separating the resulting 1,3-butadiene. Preferably, therefore, n-butane is removed as much as possible prior to the reaction, especially to a content of not more than 5% by weight.

It is an object of this invention therefore to provide at low costs large amounts of butene-1 and butene-2 having a high purity suitable for use in the aforesaid applications and being substantially free from hazardous impurities.

The $C_4$ hydrocarbon fraction to be treated by the process of this invention usually denotes a product obtained by removing 1,3-butadiene and isobutylene from $C_4$ hydrocarbons formed as by-products in the steam cracking of naphtha, or a product obtained by removing isobutylene from $C_4$ hydrocarbons formed as by-products in the catalytic cracking of petroleum, but is not limited to these specific examples. Removal of 1,3-butadiene from these $C_4$ hydrocarbons can be usually carried out by extraction in accordance with the CAA method (the cuprammonium acetate method), or an extractive distillation method using an extracting polar solvent (e.g., dimethylformamide, dimethylacetamide, N-methylpyrrolidone, and acetonitrile). On the other hand, the removal of isobutylene can be effected by a classical extracting method using sulfuric acid, or a recently developed etherification method using an aliphatic alcohol. For example, A. Clementi of ASSORNI (Association for Scientific Research of ENI Group Companies) of Italy reported in Hydrocarbon Processing, December 1979, pages 109-113 that by contacting a mixture of a $C_4$ hydrocarbon fraction and methanol with an acid catalyst (e.g., an ion exchange resin having a sulfo group), isobutylene is etherified almost completely, and remains in the $C_4$ hydrocarbon fraction in a concentration of as low as 0.1% or below.

Table 2 illustrates the composition of a $C_4$ hydrocarbon residue obtained after removing 1,3-butadiene and isobutylene.

TABLE 2

Compositions of $C_4$ hydrocarbon fractions and their solubility in dimethylformamide

| Component | Boiling point (°C.) | Composition of the $C_4$ hydrocarbon fraction | | Solubility in dimethylformamide (vol/vol/1 atm.) |
|---|---|---|---|---|
| | | Catalytic cracking | Steam cracking | |
| Propane | −42.1 | 1.8 | 0.2 | 4.0 (25° C.) |
| Propylene | −47.7 | 1.0 | 0.3 | 8.2 (25° C.) |
| iso-Butane | −11.5 | 42.7 | 5.3 | 9.2 (20° C.) |
| n-Butene | −0.5 | 12.7 | 22.6 | 16.5 (20° C.) |
| iso-Butene | −6.6 | 0.1 | 0.1 | 28.0 (20° C.) |
| Butene-1 | −6.5 | 17.8 | 37.4 | 24.6 (20° C.) |
| trans-Butene-2 | +0.3 | 13.7 | 15.7 | 35.5 (20° C.) |
| cis-Butene-2 | +3.7 | 9.9 | 13.8 | 51 (20° c.) |
| 1,3-Butadiene | −4.7 | 0.3 | 0.8 | 83.4 (20° C.) |
| Methylacetylene | −23.2 | — | 0.3 | 85 (20° C.) |
| 1,2-Butadiene | +10.3 | — | 1.2 | 160 (20° C.) |
| Vinylacetylene | — | — | 1.8 | 350 (20° C.) |
| $C_5$ | — | — | 0.5 | — |
| | | 100.0 | 100.0 | |

The present inventors have found that when a $C_4$ hydrocarbon fraction having a similar composition to those shown in Table 2 is treated by a process comprising a combination of two extractive distillation steps using a polar solvent, particularly dimethylformamide (DMF), and two ordinary distillation steps, it is possible to obtain butene-1 substantially free from diolefinic and acetylenic hydrocarbons and water which are detrimental to its use as a comonomer for ethylene polymer formation or as a monomer for production of polybutene-1, and simultaneously a cis-butene-2/trans-butene-2 mixture suitable as a material for the production of 1,3-butadiene by oxidative dehydrogenation.

Thus, according to this invention, there are provided two separating and purifying processes.

A first process is achieved by a combination of the following steps A to D.

STEP A

A $C_4$ hydrocarbon fraction is subjected to a first extractive distillation operation using a polar solvent to remove isobutane and n-butane as overhead product and a mixture of butene-1, cis-butene-2, trans-butene-2 and as impurities, diolefinic and/or acetylenic hydrocarbons as a bottom product.

STEP B

The overhead product obtained in step A is subjected to a first distillation operation to obtain a fraction consisting mainly of butene-1 and diolefinic and/or acetylenic hydrocarbons from the top of the column and a cis-butene-2/trans-butene-2 mixture from the bottom of the column.

STEP C

The fraction obtained in step B is subjected to a second extractive distillation operation to remove the diolefinic and/or acetylenic hydrocarbons entrained in butene-1 as an overhead product, and butene-1 as a bottoms product.

STEP D

Water remaining in a tiny amount in butene-1 is removed by a second distillation operation. Since water forms a minimum boiling azeotrope with butene-1, it distills out from the top of the column, and purified butene-1 is obtained from the bottom of the column.

A preferred embodiment of the first process is specifically described with reference to a flowsheet shown in FIG. 1. A $C_4$ hydrocarbon fraction containing butene-1, butene-2, etc. is fed into the middle of a first extractive distillation column A-1 having 100 trays through a line 1, and a polar solvent is fed into the distillation column several trays below its top. Thus, a first extractive distillation operation is carried out. From the top of the column, isobutane and n-butane distill out through a line 3. The distillation column can be operated at a column inside pressure of 1 to 15 atmospheres and a column bottom temperature of 100° to 180° C. From the bottom of the column, butene-1, butene-2, diolefinic hydrocarbons and acetylenic hydrocarbons are withdrawn together with the solvent, and are fed into the top of a first stripping column A-2 through a line 4. In the first stripping column A-2, the $C_4$ hydrocarbons are separated from the polar solvent. The first stripping column A-2 can usually be operated at a column inside pressure of 1 to 2 atmospheres and a column bottom temperature corresponding to the boiling point of the solvent at the pressure employed. From the top of the column, butene-1, butene-2, diolefinic hydrocarbons and acetylenic hydrocarbons are taken out through a line 5, pressurized by a compressor 6, and then fed into a first distillation column B through a line 7. Only the polar solvent is withdrawn from the bottom of the first stripping column A-2, and recycled to the column A-1 through a line 8.

The first distillation column B having 100 trays can be operated at a column inside pressure of 1 to 15 atmospheres and a column bottom temperature corresponding to the boiling point of the hydrocarbon mixture at the pressure employed. From the top of the column, butene-1, diolefinic hydrocarbons and acetylenic hydrocarbons are withdrawn through a line 9 and fed into the middle of a second extractive distillation column C-1. From the bottom of the first distillation column B, cis-butene-2 and trans-butene-2 are withdrawn with small amounts of diolefinic and acetylenic hydrocarbons through a line 10.

A polar solvent is fed through a line 11 into the second extractive distillation column C-1 having 100 trays at a site several trays below its top, and it is contacted with butene-1 fed into the middle of the column to perform a second extractive distillation operation. The second extractive distillation column C-1 can be operated at a column inside pressure of 1 to 15 atmospheres and a column bottom temperature of 100° to 160° C. From the top of the column, highly pure butene-1 is withdrawn through a line 12, and fed into the middle of a second distillation column D. From the bottom of the second extractive distillation column C-1, diolefinic and acetylenic hydrocarbons are withdrawn together with the solvent, and fed into the top of a second stripping column C-2 where the diolefinic and acetylenic hydrocarbons are separated from the solvent. The second stripping column C-2 can usually be operated at a column inside pressure of 1 to 2 atmospheres and a column bottom temperature corresponding to the boiling point of the solvent at the pressure employed. From the top of the second second stripping column C-2, the diolefinic and acetylenic hydrocarbons are discharged through a line 14. From its bottom, only the solvent is withdrawn and recycled to the second extractive distillation column C-1 through a line 15.

The second distillation column D having 30 trays can usually be operated at a column inside pressure of 1 to 15 atmospheres and a column bottom temperature corresponding to the boiling point of the hydrocarbon mixture at the pressure employed. A very small amount of water is taken out from the top of the second distillation column D through a line 16. Highly pure butene-1 as a product is withdrawn from the bottom of the column D through a line 17.

A second process is achieved by a combination of the following steps A to D.

STEP A

A $C_4$ hydrocarbon fraction is subjected to a first extractive distillation operation using a polar solvent to remove isobutane and n-butane as an overhead product and a mixture of butene-1, cis-butene-2, trans-butene-2 and as impurities, diolefinic and/or acetylenic hydrocarbons as a bottoms product.

STEP B

The overhead product obtained in step A is subjected to a second extractive distillation operation using a polar solvent to obtain a product containing butene-1 and butene-2 as main ingredients from the top of the column and a mixture of diolefinic and/or acetylenic hydrocarbons as the product from the bottom of the column.

STEP C

The product from the top of the column obtained in step B is subjected to a first distillation operation to obtain butene-1 from the top of the column and purified butene-2 from the bottom of the column.

STEP D

Water remaining in a tiny amount in butene-1 is removed by a second distillation operation. Since at this time water forms a minimum boiling azeotrope with butene-1, it distills out from the top of the column. Purified butene-1 is obtained from the bottom of the column.

A preferred embodiment of the second process is specifically described below with reference to a flowsheet shown in FIG. 2. A $C_4$ hydrocarbon fraction containing butene-1, butene-2, etc. is fed into the middle of a first extractive distillation column A-1 having 100 trays through a line 1. A polar solvent is fed into the column several trays below its top through a line 2. Thus, a first extractive distillation operation is carried out. From the top of the column, isobutane and n-butane distill out through a line 3. The column can be operated at a column inside pressure of 1 to 15 atmospheres and a column bottom temperature of 100° to 180° C. From the bottom of the column, butene-1, butene-2, diolefinic hydrocarbons and acetylenic hydrocarbons are withdrawn together with the solvent, and fed into the top of a first stripping column A-2 through a line 4. In the first stripping column A-2, the $C_4$ hydrocarbons are separated from the polar solvent. The first stripping column A-2 can usually be operated at a column inside pressure of 1 to 2 atmospheres and a column bottom temperature corresponding to the boiling point of the solvent at the pressure employed. From the top of the column, butene-1, butene-2, diolefinic hydrocarbons and acetylenic hydrocarbons are withdrawn through a line 5, pressurized by a compressor 6, and then fed into a second extractive distillation column B-1 through a line 7. Only the solvent is withdrawn from the bottom of the first stripping column A-2, and recycled to the column A-1 through a line 8.

A polar solvent is fed through a line 9 into the second extractive distillation column B-1 having 100 trays at a site several trays below its top, and contacted with butene-1, butene-2, diolefinic hydrocarbons and acetylenic hydrocarbons fed into the middle of the column through the line 7, whereby a second extractive distillation operation is carried out. The second extractive distillation column can be operated at a column inside pressure of 1 to 15 atmospheres and a column bottom temperature of 100° to 160° C. From the top of the second extractive distillation column B-1, a mixture of butene-1 and butene-2 is withdrawn through a line 10, and fed into the middle of a first distillation column C. From the bottom of the column, diolefinic and acetylenic hydrocarbons are withdrawn together with the solvent, and fed into the top of a second stripping column B-2 where the diolefinic and acetylenic hydrocarbons are separated from the polar solvent. The second stripping column B-2 can usually be operated at a column inside pressure of 1 to 2 atmospheres and a column bottom temperature corresponding to the boiling point of the solvent at the pressure employed. From the top of the column, the diolefinic and acetylenic hydrocarbons are discharged through a line 12. From the bottom of the column, only the solvent is withdrawn and recycled to the column B-1 through a line 13.

The first distillation column C having 100 trays can usually be operated at a column inside pressure of 1 to 15 atmospheres and a column bottom temperature corresponding to the boiling point of the hydrocarbon mixture at the pressure employed. From the top of the column, butene-1 is withdrawn through a line 14, and fed into the middle of the second distillation column D. From the bottom of the column, purified cis-butene-2 and trans-butene-2 are withdrawn through a line 15.

The second distillation column D having 30 trays can usually be operated at a column inside pressure of 1 to 15 atmospheres and a column bottom temperature corresponding to the boiling point of the hydrocarbon mixture at the pressure employed. From the top of the column, a very small amount of water is withdrawn through a line 16. Highly pure butene-1 as a product is withdrawn from the bottom of the column through a line 17.

The polar solvent used in this invention may be any of those polar solvents which are generally used for the extractive distillation of 1,3-butadiene from a $C_4$ hydrocarbon fraction. Examples include N-alkyl-substituted lower fatty acid amides, furfural, N-methylpyrrolidone, formylmorpholine, and acetonitrile. The N-alkyl-substituted lower fatty acid amides include dimethylformamide, diethylformamide and dimethylacetamide. These amide solvents are preferred for the object of this invention since they have an excellent solubility, an excellent relative volatility and a moderate boiling point in an anhydrous condition. Table 3 shows the relative volatilities of $C_4$ hydrocarbons in various polar solvents. Among the above-exemplified polar solvents dimethylformamide is most preferred.

These polar solvents may be used singly or as a mixture of two or more. Together with the polar solvent, polymerization inhibitors for inhibiting the polymerization of diolefinic and acetylenic hydrocarbons, antioxidants, antifoamers, etc. may be used. Various types of polymerization inhibitors can be used which have the ability to inhibit polymerization and/or to induce chain transfer. Examples include t-butylcatechol, sulfur sodium nitrite, furfural, benzaldehyde, and aromatic nitro compounds. They may be used either singly or as a mixture of two or more.

TABLE 3

| Relative volatilities in various polar solvents (data obtained at 50° C. with infinite dilution) | | | |
|---|---|---|---|
| | Solvent | | |
| | Dimethyl-formamide | Diethyl-formamide | N—methylpyrrolidone |
| Boiling Point (°C.) | 153 | 177.5 | 202 |
| iso-Butane | 5.3 | 5.2 | 7.25 |
| n-Butane | 3.8 | 3.6 | 4.30 |
| Butene-1 | 2.4 | 2.3 | 2.60 |
| trans-Butene-2 | 1.9 | 1.8 | 2.00 |
| cis-Butene-2 | 1.7 | 1.5 | 1.63 |
| 1,3-Butadiene | 1.0 | 1.0 | 1.00 |

The following examples illustrate the present invention more specifically.

EXAMPLE 1

Using the apparatus shown in FIG. 1, the following experiment was carried out.

A starting material having the composition shown in Table 4 was fed at a rate of 22.5 kg/hour into the middle of the first extractive distillation column A-1 having 100 trays through line 1, and extractively distilled under the following conditions.

Polar solvent: fed at a rate of 225 kg/hour
Reflux liquid: 22 kg/hour
Pressure of the top of the column: 3.5 kg/cm² (G)
Temperature of the top of the column: 45° C.
Temperature of the bottom of the column: 139° C.

As a result, a gas having the composition shown in Table 4 was obtained at a rate of 16.4 kg/hour from line 5 of the first stripping column A-2. Removal of butanes was achieved nearly completely.

The resulting gas was forced into the middle of the first distillation column B having 100 trays, and distilled at a column top pressure of 3.3 kg/cm² (G) and a column top temperature of 37° C. with a reflux ratio of 9. As a result, a butene-2 mixture having the composition shown in Table 4 was obtained at a rate of 7.65 kg/hour from the bottom of the column through line 10.

All of the gas from the top of the column which contained butene-1 as a main ingredient was introduced into the middle of the second extractive distillation column C-1 having 100 trays, and extractively distilled at a column top pressure of 3.3 kg/cm² (G), a column top temperature of 37° C. and a column bottom temperature of 145° C. using a polar solvent fed at a rate of 60 kg/hour and maintaining the flow rate of the reflux liquid at 8 kg/hour. From the top of the column, butene-1 substantially free from diolefinic and acetylenic hydrocarbons was obtained.

All of the butene-1 thus obtained was introduced into the middle of the second distilling column D having 30 trays to remove water. After operating at a column top pressure of 3.3 kg/cm² (G) and a column top temperature of 37° C., butene-1 having the composition shown in Table 4 and substantially free from water was obtained at a rate of 7.65 kg/hour from the bottom of the column through line 17.

The polar solvent used was a mixture of anhydrous dimethylformamide with 0.1% by weight of nitrobenzene and 0.05% by weight of sodium nitrite.

TABLE 4

| | Compositions (% by weight) | | | |
|---|---|---|---|---|
| Composition | Starting C₄ hydrocarbon fraction from line 1 | Gas from line 5 | Butene-2 mixture from line 10 | Butene-1 from line 17 |
| iso-Butane | 5.8 | — | — | — |
| n-Butane | 21.6 | 1.4 | 2.6 | 0.17 |
| Butene-1 | 37.4 | 50.82 | 1.9 | 99.17 |
| iso-Butene | 0.1 | 0.14 | 0.0 | 0.21 |
| trans-Butene-2 | 19.7 | 26.8 | 57.7 | 0.35 |
| cis-Butene-2 | 13.2 | 17.9 | 36.8 | 0.10 |
| 1,3-Butadiene | 1.5 | 2.0 | 0.8 | 85 (ppm) |
| Methylacetylene | 0.6 | 0.8 | 0.0 | 2 (ppm) |
| Ethylacetylene | 0.1 | 0.14 | 0.2 | 1 (ppm) |
| | 100.0 | 100.0 | 100.0 | 100.0 |

EXAMPLE 2

Using the apparatus shown in FIG. 2, the following experiment was carried out.

A starting material having the composition shown in Table 5 was fed at a rate of 22.5 kg/hour into the middle of the first extractive distillation column A-1 having 100 trays through line 1, and extractively distilled at a column top pressure of 3.5 kg/cm² (G), a column top temperature of 45° C. and a column bottom temperature of 139° C. using a polar solvent solvent fed at a rate of 225 kg/hour and maintaining the flow rate of the reflux liquid at 22 kg/hour. As a result, a gas having the composition shown in Table 5 was obtained at a rate of 16.4 kg/hour from the top of the first stripping column. Removal of butanes was achieved nearly completely.

The gas from the line 5 was forced into the middle of the second extractive distillation column B-1 having 100 trays at a rate of 16.4 kg/hour, and extractively distilled at a column top pressure of 3.3 kg/cm² (G), a column top temperature of 40° C. and a column bottom temperature of 150° C. using a polar solvent fed at a rate of 110 kg/hour and maintaining the flow rate of the reflux liquid at 16 kg/hour. As a result, a butene-1/butene-2 mixture substantially free from diolefinic and acetylenic hydrocarbons was obtained from the top of the column at a rate of 15.3 kg/hour.

All of the mixture was introduced into the middle of the first distillation column C having 100 trays, and distilled at a reflux ratio of 9, a column top pressure of 3.3 kg/cm² and a column top temperature of 37° C. As a result, butene-2 having the composition shown in Table 5 was obtained at a rate of 7.2 kg/hour from the bottom of the column through line 15. From the top of the column, butene-1 was obtained at a rate of 8.0 kg/hour.

All the butene-1 thus obtained was introduced into the middle of the second distillation column D, and distilled at a column top pressure of 3.3 kg/cm² (G) and a column top temperature of 37° C. As a result, highly pure butene-1 having the composition shown in Table 5 and being substantially free from water was obtained from the bottom of the column through line 17.

The polar solvent used was a mixture of anhydrous dimethylformamide with 0.1% by weight of nitrobenzene and 0.05% by weight of sodium nitrite.

TABLE 5

| | Composition (% by weight) | | | |
|---|---|---|---|---|
| Composition | Starting C₄ hydrocarbon fraction from line 1 | Gas from line 5 | Butene-2 from line 15 | Butene-1 from line 17 |
| iso-Butane | 5.8 | — | — | — |
| n-Butane | 21.6 | 1.4 | 2.7 | 0.14 |
| Butene-1 | 37.4 | 50.82 | 1.9 | 99.30 |
| iso-Butene | 0.1 | 0.14 | 0.0 | 0.20 |
| trans-Butene-2 | 19.7 | 26.8 | 57.5 | 0.28 |
| cis-Butene-2 | 13.2 | 17.9 | 37.9 | 0.08 |
| 1,3-Butadiene | 1.5 | 2.0 | 20 (ppm) | 72 (ppm) |
| Methylacetylene | 0.6 | 0.8 | 0 (ppm) | 2 (ppm) |
| Ethylacetylene | 0.1 | 0.14 | 2 (ppm) | 1 (ppm) |
| | 100.0 | 100.0 | 100.0 | 100.0 |

What is claimed is:

1. A process for separating highly pure butene-2 and highly pure butene-1 substantially free from diolefinic and acetylenic hydrocarbons from a C₄ hydrocarbon fraction containing isobutane, n-butane, butene-1, butene-2, and at least one hydrocarbon selected from diolefinic hydrocarbons and acetylenic hydrocarbons, which comprises (1) as a first extractive distillation step, treating the C₄ hydrocarbon fraction with a polar solvent in a first extractive distillation column to separate it into an overhead product containing isobutane and n-butane as main ingredients and a bottoms product containing butene-1, butene-2 and said at least one hydrocarbon as main ingredients, (2) as a first distillation step, introducing the bottoms product from step (1) into a first distillation column to obtain a fraction containing butene-1, and said at least one hydrocarbon as main ingredients from the top of the column and purified butene-2 from the bottom of the column, (3) as a second extractive distillation step, introducing the fraction obtained in step (2) containing butene-1 as main ingredients into a second extractive distillation column and treating it with a polar solvent to separate it into an overhead product containing butene-1 as a main ingredient and a bottoms product containing said at least one hydrocarbon as main ingredients, and (4) as a second distillation step, introducing the overhead product obtained in step (3) into a second distillation column to remove a tiny amount of water from the top of the column and obtain purified butene-1 from the bottom of the column.

2. A process for separating highly pure butene-2 and highly pure butene-1 substantially free from diolefinic and acetylenic hydrocarbons from a $C_4$ hydrocarbon fraction containing isobutane, n-butane, butene-1, butene-2, and at least one hydrocarbon selected from diolefinic hydrocarbons and acetylenic hydrocarbons, which comprises (1) as a first extractive distillation step, treating the $C_4$ hydrocarbon fraction with a polar solvent to separate it into an overhead product containing isobutane and n-butane as main ingredients and a bottoms product containing butene-1, butene-2 and said at least one hydrocarbon as main ingredients, (2) as a second extractive distillation step, introducing the bottoms product from step (1) into a second extractive distillation column and treating it with a polar solvent to separate it into an overhead product containing butene-1 and butene-2 as main ingredients and a bottoms product containing said at least one hydrocarbon as main ingredients, (3) as a first distillation step, introducing the overhead product step (2) into a first distillation column to obtain butene-1 from the top of the column and purified butene-2 from the bottom of the column, and (4) as a second distillation step, introducing butene-1 from step (3) into a second distillation column to remove a tiny amount of water from the top of the column and obtain purified butene-1 from the bottom of the column.

3. The process of claim 1 or 2 wherein the polar solvent used in the first and second extractive distillation steps is an N-alkyl-substituted lower fatty acid amide.

* * * * *